(12) United States Patent
Moon et al.

(10) Patent No.: US 11,329,242 B2
(45) Date of Patent: May 10, 2022

(54) LIGHTING DEVICE COMPRISING PLURALITY OF LIGHT EMITTING LAYERS

(71) Applicant: LG Display Co., Ltd., Seoul (KR)

(72) Inventors: Jaemin Moon, Seoul (KR); Jina You, Seoul (KR); JungHyoung Lee, Daejeon (KR); SunHee Lee, Seoul (KR); JangDae Youn, Daejeon (KR)

(73) Assignee: LG DISPLAY CO., LTD., Seoul (KR)

( * ) Notice: Subject to any disclaimer, the term of this patent is extended or adjusted under 35 U.S.C. 154(b) by 44 days.

(21) Appl. No.: 16/897,132

(22) Filed: Jun. 9, 2020

(65) Prior Publication Data

US 2020/0395567 A1    Dec. 17, 2020

(30) Foreign Application Priority Data

Jun. 12, 2019   (KR) ......................... 10-2019-0069462

(51) Int. Cl.
*H01L 51/50*      (2006.01)
*H01L 51/52*      (2006.01)
*A61N 5/06*       (2006.01)

(52) U.S. Cl.
CPC ........ *H01L 51/5044* (2013.01); *A61N 5/0616* (2013.01); *H01L 51/5072* (2013.01); *H01L 51/5265* (2013.01); *H01L 51/5275* (2013.01); *A61N 2005/0653* (2013.01); *A61N 2005/0663* (2013.01)

(58) Field of Classification Search
None
See application file for complete search history.

(56) References Cited

U.S. PATENT DOCUMENTS

2001/0048703 A1\* 12/2001 Oh ..................... G11B 7/1275
                                                             372/43.01
2017/0149006 A1\* 5/2017 Park ..................... H01L 51/5072

\* cited by examiner

*Primary Examiner* — Daniel Whalen
(74) *Attorney, Agent, or Firm* — Polsinelli PC (57) ABSTRACT

A lighting device comprises a substrate including an active area; a first electrode disposed on the substrate and including a transparent conductive material; an organic material layer disposed on the first electrode and including a first light emitting layer and a second light emitting layer; and a second electrode disposed on the organic material layer and including a reflective material, wherein the first light emitting layer emits light having a first wavelength and the second light emitting layer emits light having a second wavelength, and wherein the second light emitting layer includes a first dopant absorbing the light having the first wavelength and emitting the light having the second wavelength.

16 Claims, 10 Drawing Sheets

LIGHTING DEVICE COMPRISING PLURALITY OF LIGHT EMITTING LAYERS

CROSS REFERENCE TO RELATED APPLICATION

This application claims priority from Korean Patent Application No. 10-2019-0069462, filed on Jun. 12, 2019, which is hereby incorporated by reference in its entirety.

BACKGROUND

Field of the Disclosure

The present disclosure relates to a lighting device.

Description of the Background

Skin of a person can be often damaged by aging of cells, repetition of specific expressions, continuous exposure to the external environment (ultraviolet rays, fine dust, and so on) and stress. For example, aging of cells or repetition of any specific facial expression may most likely cause wrinkles on the skin, and continuous exposure to the external environment or stress may result in various skin troubles such as acne, freckles, and the like.

Skin care for preventing or minimizing such an undesired damage to the skin is aimed at maintaining clean, soft skin without any blemishes, particularly, paying most attention to facial skin care.

In the recent years, cosmetic lighting devices, which may be attached to or worn on a user's face in use to output light, have been more often introduced in the market. Such lighting devices may be commonly provided with a plurality of light sources, so that light in a specific wavelength band can be irradiated onto the user's facial skin.

In case where a light emitting diode (LED) is adopted as a light source for such a cosmetic lighting device, a plurality of light emitting diodes, that is, point light sources, may be used. However, the use of a plurality of light emitting diodes generally makes it difficult to provide a uniform irradiation of light in the form of point light source, and so a separate light source is required for each wavelength, thereby leading to more complicated circuit configuration which essentially involves more thickness and weight.

SUMMARY

The present disclosure provides a lighting device that can implement lightweight and thinner thickness of structure as well as adjust the irradiation area of light with ease.

The present disclosure provides a lighting device capable of irradiating light having various wavelengths with a simple circuit configuration, the lighting device including an organic material layer including a first light emitting layer and a second light emitting layer.

According to an aspect of the present disclosure, a lighting device comprises a substrate including an active area, a first electrode disposed on the substrate and including a transparent conductive material, an organic material layer disposed on the first electrode, and a second electrode disposed on the organic material layer and including a reflective material.

Here, the organic material layer may include a first light emitting layer and a second light emitting layer.

Further, the light emitted by the first light emitting layer may have a first wavelength, and the light emitted by the second light emitting layer may have a second wavelength.

Furthermore, the second light emitting layer may include a first dopant absorbing the light having the first wavelength and emitting the light having the second wavelength.

The present disclosure may be arranged so that the first light emitting layer is not patterned and is disposed at least over the entire active area of the substrate, and the second light emitting layer is not patterned and is disposed at least over the entire active area of the substrate.

Here, the second light emitting layer may be positioned closer to the second electrode than the first light emitting layer.

According to another aspect, the first light emitting layer may be patterned to be formed in a first area, and the second light emitting layer may be patterned to be formed in a second area, wherein the first area and the second area may not overlap each other.

According to the present disclosure, there is provided a lighting device comprising a first light emitting layer, a second light emitting layer including a first dopant absorbing light emitted from the first light emitting layer, a first electrode including a transparent conductive material, and a second electrode including a reflective material, wherein the second light emitting layer may be positioned closer to the second electrode than the first light emitting layer, thereby providing the lighting device with improved light efficiency.

According to aspects of the present disclosure, there is further provided a lighting device with improved light efficiency, configured so that the first light emitting layer is patterned to be formed in the first area, and the second light emitting layer is patterned to be formed in the second area, the first area and the second area being not overlap with each other.

DESCRIPTION OF DRAWINGS

The above and features, and advantages of the present disclosure will be more clearly understood from the following detailed description, taken in conjunction with the accompanying drawings, in which.

DETAILED DESCRIPTION

In the following description of examples or aspects of the present disclosure, reference will be made to the accompanying drawings in which it is shown by way of illustration specific examples or aspects that can be implemented, and in which the same reference numerals and signs can be used to designate the same or like components even when they are shown in different accompanying drawings from one another. Further, in the following description of examples or aspects of the present disclosure, detailed descriptions of well-known functions and components incorporated herein will be omitted when it is determined that the description may make the subject matter in some aspects of the present disclosure rather unclear. The terms such as "including", "having", "containing", "constituting", "make up of", and "formed of" used herein are generally intended to allow other components to be added unless the terms are used with the term "only". As used herein, singular forms are intended to include plural forms unless the context clearly indicates otherwise.

Terms, such as "first", "second", "A", "B", "(A)", or "(B)" may be used herein to describe elements of the present disclosure. Each of these terms is not used to define essence, order, sequence, or number of elements etc., but is used merely to distinguish the corresponding element from other elements.

When it is mentioned that a first element "is connected or coupled to", "contacts or overlaps" etc. a second element, it should be interpreted that, not only can the first element "be directly connected or coupled to" or "directly contact or overlap" the second element, but a third element can also be "interposed" between the first and second elements, or the first and second elements can "be connected or coupled to", "contact or overlap", etc. each other via a fourth element. Here, the second element may be included in at least one of two or more elements that "are connected or coupled to", "contact or overlap", etc. each other.

When time relative terms, such as "after," "subsequent to," "next," "before," and the like, are used to describe processes or operations of elements or configurations, or flows or steps in operating, processing, manufacturing methods, these terms may be used to describe non-consecutive or non-sequential processes or operations unless the term "directly" or "immediately" is used together.

In addition, when any dimensions, relative sizes etc. are mentioned, it should be considered that numerical values for an elements or features, or corresponding information (e.g., level, range, etc.) include a tolerance or error range that may be caused by various factors (e.g., process factors, internal or external impact, noise, etc.) even when a relevant description is not specified. Further, the term "may" fully encompasses all the meanings of the term "can".

Figure 1:
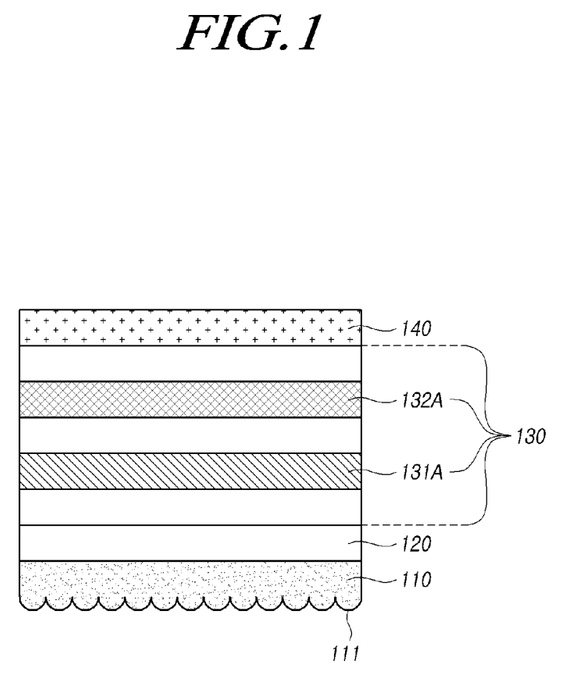
FIG. 1 is a cross-sectional view schematically illustrating a lighting device according to the present disclosure.

FIG. 1 is a cross-sectional view schematically illustrating a lighting device according to the aspects of the present disclosure.

Referring now to FIG. 1, the lighting device according to the aspects of the present disclosure may include a substrate 110, a first electrode 120, an organic material layer 130, and a second electrode 140.

The first electrode 120 may be disposed on the substrate 110, the organic material layer 130 may be located on the first electrode 120, and the second electrode 140 may be located on the organic material layer 130.

The first electrode 120, the organic material layer 130, and the second electrode 140 may be referred to as an organic light emitting diode (OLED) or a light emitting element.

The substrate 110 may include an active region and a non-active region, wherein the active region may be a region in which the organic light emitting device is disposed, and the non-active region may be disposed outside the active region. A plurality of pad electrodes electrically connected to the outside may be disposed in the non-active region. A signal (for example, DC voltage) may be applied to the organic light emitting device disposed in the active area through the non-active area, so that light can be emitted from the organic light emitting device.

The substrate 110 may be formed of a transparent material. When the substrate 110 is formed of such a transparent material, the light emitted from the lighting device may be extracted out of the lighting device through the substrate 110.

The type of the substrate 110 may be not particularly limited, and it may be formed of, for example, a glass substrate or a plastic substrate. In particular, when some flexibility is required for the lighting device, a polymer plastic substrate may be used.

On one surface of the substrate 110, a plurality of protrusions 111 formed repeatedly may be provided. The plurality of protrusions may be a micro-lens array (MLA), which may be formed for the purpose of increasing the light that can be extracted out through the substrate 110. When the one surface of the substrate 110 is formed in the shape of a lens, the angle of incident light to the substrate can be changed to mitigate total reflection of the light at the interface between the substrate 110 and the air.

The substrate 110 may be a high refractive substrate with a high refractive index. For example, the refractive index of the organic light emitting element may be about 1.6 to 1.9, the refractive index of the substrate 110 may be 1.6 to 1.9, wherein the refractive index of the organic light emitting element may be substantially the same as that of the substrate 110, or the refractive index of the substrate 110 may have a higher refractive index. When the substrate 110 with a high refractive index is used, it is possible to prevent the light emitted from the organic light emitting element from being total-reflected from the substrate and the light being trapped in between the organic light emitting element and the substrate.

The first electrode 120 may be positioned on the substrate 110. For example, when the aforementioned micro-lens array is formed on one surface of the substrate 110, the first electrode 120 may be positioned on the opposite side of the surface of the substrate on which the micro-lens array is formed.

The first electrode 120 may be an anode electrode. Therefore, holes may be supplied from the first electrode 120 to the organic material layer 130.

The first electrode 120 may include a transparent conductive material. For example, the first electrode 120 may include either one of indium tin oxide (ITO), indium zinc oxide (IZO), and indium gallium zinc oxide (IGZO) as the transparent conductive material.

The first electrode 120 including the transparent conductive material as described above, may be a transparent electrode having light transmittance of 80% or more. When the first electrode is a transparent electrode, the light emitted from the organic material layer may pass through the first electrode and then be extracted out of the light emitting diode element.

The second electrode 140 may be positioned on the organic material layer 130, wherein the second electrode 140 may be, for instance, a cathode electrode. Therefore, the organic material layer 130 may be disposed between the first electrode 110 and the second electrode 140, wherein holes and electrons can be supplied to the organic material layer 130 from the first electrode 110 and the second electrode 140.

The second electrode 140 may further include a reflective material. The reflective material may be of any one of metals such as e.g., aluminum (Al), silver (Ag), molybdenum (Mo), copper (Cu) or silver (Ag), and alloys such as e.g., titanium molybdenum (MoTi), although not limited thereto.

The reflectivity of the second electrode 140 may be 50% or more, but it is not limited thereto.

When the first electrode 120 is a transparent electrode including the transparent conductive material and the second electrode 140 is a reflective electrode including the reflective material, light extraction from the light emitting diode element can be improved by micro-cavity effect. Thus, the lighting device according to the aspects of the present disclosure can improve outputting of light emitted from the first light emitting layer 131A and the second light emitting layer 132A owing to such micro-cavity effect.

The organic material layer 130 may be disposed on the first electrode 120. Since the organic material layer 130 is positioned on the first electrode 120 and the second electrode 140 is positioned on the organic material layer 130, those holes and electrons can be transferred to the organic material layer 130, thereby leading to light emission.

The organic material layer 130 may include an organic material, and it may mean one or multiple layers through which the holes and electrons are supplied from the first electrode 120 and the second electrode 140.

The organic material layer 130 may include one or more light emitting layers. The light emitting layer may refer to a layer from which light is emitted due to bonding of holes and electrons, wherein the light emitting layer may include, for instance, a host material and a dopant material.

The organic material layer 130 may include a first light emitting layer 131A and a second light emitting layer 132A, wherein the light emitted by the first light emitting layer 131A may have a first wavelength $\lambda 1$, and the light emitted by the second light emitting layer 132A may have a second wavelength $\lambda 2$. Here, the first wavelength $\lambda 1$ and the second wavelength $\lambda 2$ may be understood as a specific range of values. Therefore, the light emitted from the first light emitting layer 131A has a wavelength corresponding to the first wavelength $\lambda 1$, falling in the specific range of the first wavelength. Likewise, the relationship of the second light emitting layer 132A and the second wavelength $\lambda 2$ may be similar to that described above.

Although FIG. 1 shows that the second light emitting layer 132A is seemingly positioned on the first light emitting layer 131A, the aspects of the present disclosure as disclosed herein are not intended to limit that the second light emitting layer 132A is located on the first light emitting layer 131A. Rather, in some aspects of the present disclosure as described below, the first light emitting layer 131A and the second light emitting layer 132A may be disposed on a certain layer, so that these light emitting layers are arranged in a different area not to overlap each other.

Figure 2:
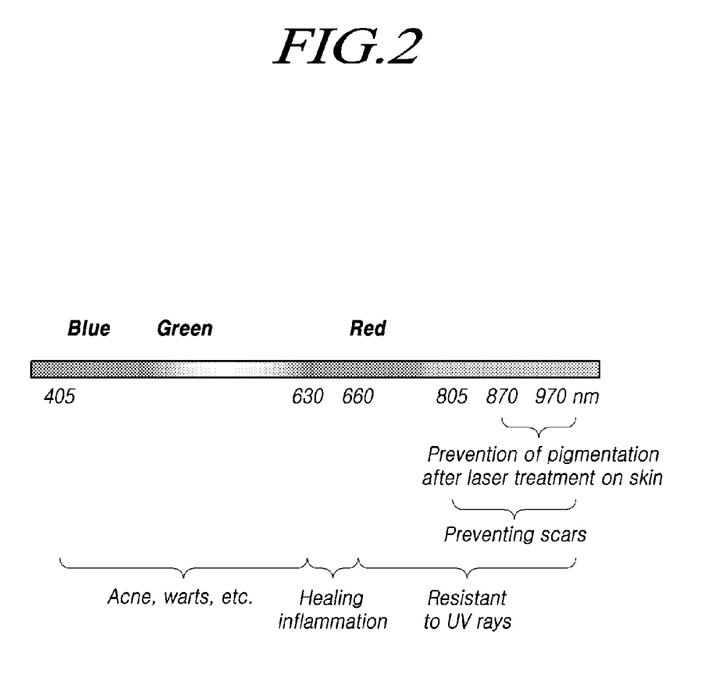
FIGS. 2 and 3 are schematic microscopic views for explaining the cosmetic effect on skin according to the wavelengths of light.

FIG. 2 shows a schematic view for explaining the cosmetic effect on skin according to the wavelengths of light.

Referring to FIG. 2, it is seen that light having a wavelength of about 630 nm to 700 nm may be effective in healing inflammation. Further, light having a wavelength of about 700 nm to 1000 nm may have an effect on skin care, such as, for example, improved resistance to ultraviolet rays, prevention of scarring, and prevention of pigmentation after skin laser treatment.

Figure 3:
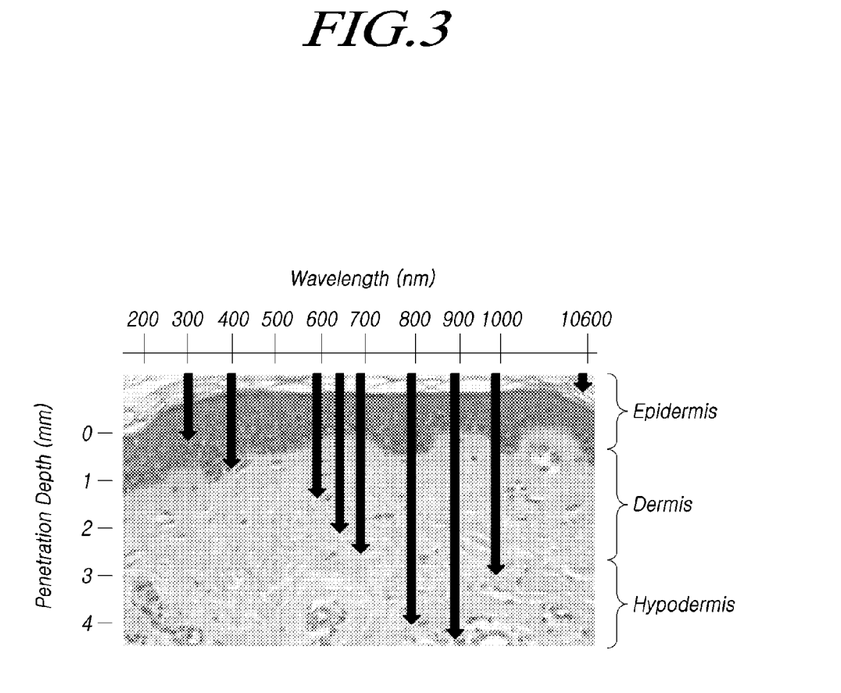

FIG. 3 shows a schematic microscopic view for explaining the cosmetic effect on skin according to the wavelengths of light.

Referring to FIG. 3, it is seen that light having a wavelength of about 600 nm to 700 nm may penetrate into a dermis layer of the skin to render the aforementioned cosmetic effect to the skin. Further, light having a wavelength of about 800 nm to 1000 nm may penetrate into hypodermis of the skin to render such a cosmetic effect on the skin. As such, it will be appreciated that such a cosmetic lighting device can use light with the above-described range of wavelength.

The first wavelength may be, for example, in the range of 550 nm to 800 nm, 550 nm to 750 nm, or 550 nm to 670 nm. When the first wavelength falls within the above-described range, the light emitted from the first light emitting layer may render a good skin care effect such as inflammation healing and others.

The second wavelength may be, for example, in the range of 700 nm to 1000 nm, 750 nm to 950 nm, or 750 nm to 880 nm. When the second wavelength falls within in the above-described range, light emitted from the second light emitting layer may have a skin care effect such as e.g., healing of inflammation and improved resistance to ultraviolet rays.

Figure 4:
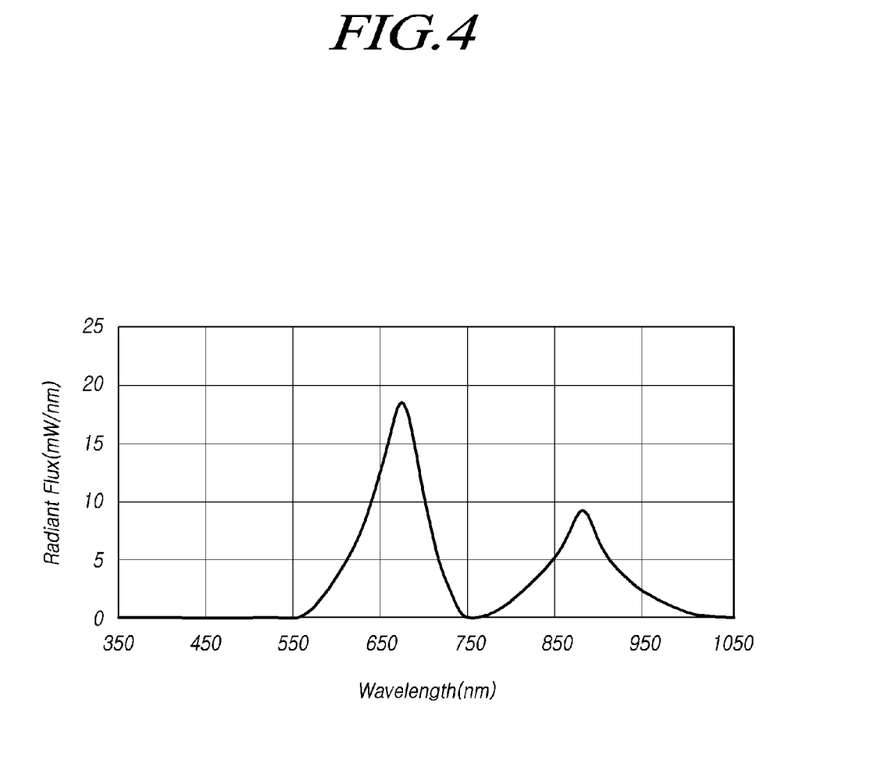
FIG. 4 is a graphic view for explaining the wavelength of light emitted from the first light emitting layer and the second light emitting layer according to the present disclosure.

FIG. 4 is a graphic view for explaining the wavelength of light emitted from the first light emitting layer and the second light emitting layer according to the aspects of the present disclosure.

Referring to FIG. 4, light emitted from the first light emitting layer may have a wavelength of about 550 nm to 800 nm, and light emitted from the second light emitting layer may have a wavelength of about 700 nm to 1000 nm. Therefore, the lighting device according to the aspects of the present disclosure can make irradiation of the light with the above-described cosmetic effect onto the skin, and its light output can be improved by the micro-cavity effect, thereby rendering an excellent skin care effect.

The second light emitting layer may include a first dopant that absorbs light having a first wavelength and emits light having a second wavelength. When it is stated that the dopant absorbs the light having the first wavelength, it may mean to absorb light having a wavelength corresponding to a whole or part of the range of the first wavelength. Further, when it is stated that the dopant emits light having the second wavelength, it may mean to emit light having a wavelength corresponding to a whole or a part of the range of the second wavelength.

Figure 5:
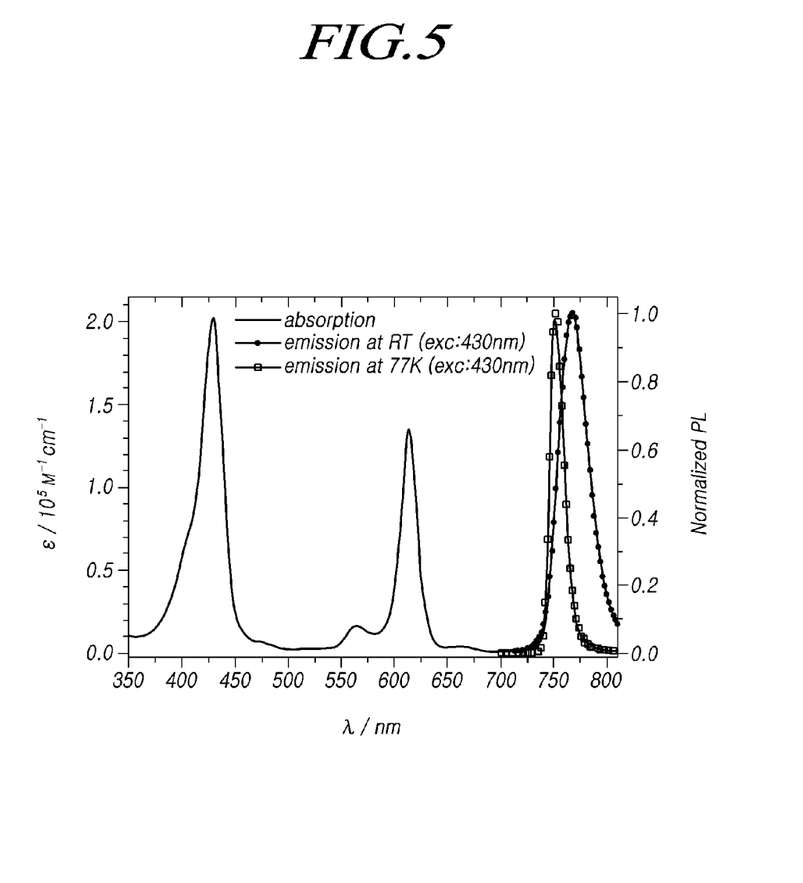
FIG. 5 is a graphic view for explaining the wavelength of light absorbed by and the wavelength of light emitted from a dopant according to the present disclosure.

Here, the first dopant may be, for example, Pt(TPBP) (Pt-tetraphenyltetrabenzoporphyrin). FIG. 5 is a graphic view for explaining the wavelengths of light that Pt(TPBP) absorbs and emits.

Referring to FIG. 5, the light emitted by Pt(TPBP) may be in the range of about 700 nm to 900 nm in wavelength. In some aspects, the second wavelength may be in the range of 700 nm to 1000 nm, so it can be seen that Pt(TPBP) emits the light having the second wavelength according to FIG. 5. Accordingly, according to some aspects of the present disclosure, it is possible to provide a lighting device capable of outputting the light having an excellent cosmetic effect by using Pt(TPBP) as a first dopant.

The light absorbed by Pt(TPBP) may be about 370 nm and about 700 nm of wavelength when referring to the peak in the wavelength axis. In some aspects, the first wavelength may be in the range of 550 nm to 800 nm, so it can be seen that according to FIG. 5, Pt(TPBP) absorbs the light having the first wavelength.

Accordingly, when using a first dopant absorbing the light having the first wavelength for the second light emitting layer, as is in Pt (TPBP) taken as an example, at least part of the light emitted from the first light emitting layer can be absorbed to the first dopant included in the second light emitting layer. However, the aspects of the present disclosure can provide a lighting device capable of emitting the light of 550 nm to 700 nm wavelength with excellent cosmetic effect on the skin, as well as emitting the light of 750 nm to 900 nm wavelength with excellent cosmetic effect on the skin using the aforementioned first dopant.

Figure 6:
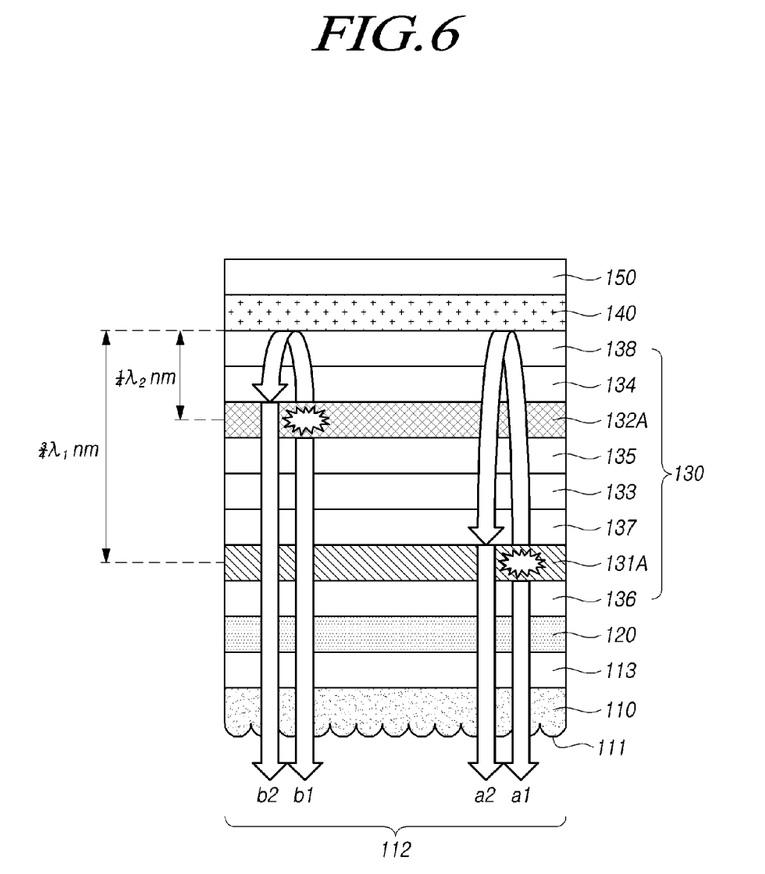
FIGS. 6 to 8 each are schematic cross-sectional views of a lighting device according to the present disclosure.

FIG. 6 shows a schematic cross-sectional view of a lighting device according to the aspects of the present disclosure.

Referring to FIG. 6, a lighting device according to the aspects of the present disclosure may include a substrate 110, a first electrode 120, an organic material layer 130, a second electrode 140, and an encapsulation layer 150.

A plurality of protrusions 111 as described above may be integrally provided on a rear surface of the substrate 110. In addition, a barrier layer 113 may be formed on a surface opposite to the rear surface of the substrate 110. Here, the barrier layer 113 may serve to block external moisture and oxygen that can penetrate through the substrate 110 formed of e.g., a flexible polymer resin.

The organic material layer 130 may include a first light emitting layer 131A and a second light emitting layer 132A described above.

The first light emitting layer 131A may be not patterned and may be disposed at least over the entire active area 112 of the substrate 110. The first light emitting layer 131A being not patterned may mean that the first light emitting layer 131A is formed, for example, by entire deposition on the substrate without a patterning process.

The second light emitting layer 132A may be not patterned and may be disposed at least over the entire active area 112 of the substrate. The second light emitting layer 132A being not patterned may mean that the second light emitting layer 132A is formed, for example, by entire deposition on the substrate without a patterning process.

The second light emitting layer 132A may be positioned closer to the second electrode 140 than the first light emitting layer 131A. For example, a charge generation layer 133 may be disposed between the second light emitting layer 132A and the first light emitting layer 131A, and the second light emitting layer 132A may be disposed adjacent to the second electrode 140.

The light emitted from the first light emitting layer 131A may be extracted (a1) out of the lighting device through the first electrode 120, which is a transparent electrode, and the light is then reflected off the second electrode 140, which is a reflective electrode, to be extracted (a2) out of the lighting device. At this point, the intensity of the light (a1) that passes through the transparent electrode to be extracted out of the lighting device is greater than the intensity of the light (a2) that is reflected off the reflection electrode to be extracted out of the lighting device. This is because the a path of the light (a2) reflected off the reflection electrode is longer than that of the light (a1), and further, part of the light emitted from the first light emitting layer 131A is absorbed into the first dopant included in the second light emitting layer 132A.

In case where the second light emitting layer 132A is positioned adjacent to the second electrode 140, the light (a2) reflected off and emitted from the second electrode 140, other than the light (a1) emitted from the first light emitting layer 131A through the first electrode 120, is absorbed into the first dopant included in the second light emitting layer 132A. Hence, in this case, a smaller amount of light than when the second light emitting layer 132A is located between the first light emitting layer 131A and the first electrode 120 can be absorbed into the first dopant, so it can further increase the output of light with the first wavelength.

Further, for improving the intensity of the light (a1, a2) emitted from the first light emitting layer 131A due to the micro-cavity effect, a distance between the first light emitting layer 131A and the second electrode 140 may be 0.70 to 0.80 times the first wavelength. Advantageously, the range of the wavelength may be, for example, 0.72 to 0.78 times as the first wavelength, or more advantageously, 0.74 to 0.76 times. Alternatively, the distance between the first light emitting layer 131A and the second electrode 140 may be substantially 0.75 times the first wavelength. The distance between the first light emitting layer 131A and the second electrode 140 may designate a distance from the center of the first light emitting layer 131A to the reflective surface of the second electrode 140, and the first wavelength in the aforementioned distance may be a wavelength of the light having the strongest intensity when measuring light emitted from the first light emitting layer 131A.

Then, the light emitted from the second light emitting layer 132A may be also extracted (b1) out of the lighting device through the first electrode 120 corresponding to a transparent electrode, and then reflected off the second electrode 140 corresponding to a reflective electrode to be extracted (b2) out of the lighting device.

For improving the intensity of the light (b1, b2) emitted from the second light emitting layer 132A by the micro-cavity effect, the distance between the second light emitting layer 132A and the second electrode 140 may be 0.20 to 0.30 times the second wavelength. Advantageously, the above range may be, for example, 0.22 to 0.28 times or 0.24 to 0.26 times the second wavelength. Alternatively, the distance between the second light emitting layer 132A and the second electrode 140 may be substantially 0.25 times the second wavelength. The distance between the second light emitting layer 132A and the second electrode 140 may designate a distance from the center of the second light emitting layer 131A to the reflective surface of the second electrode 140, and the second wavelength in the aforementioned distance may be a wavelength of the light having the strongest intensity when measuring light emitted from the second light emitting layer 132A.

The organic material layer 130 may include other organic material layers, in addition to the first light emitting layer 131A, the second light emitting layer 132A and the charge generation layer 133. As an example, in sequence, a first functional layer 136 may be disposed on the first electrode 120, a first light emitting layer 131A may be disposed on the first functional layer 136, a first electron transport layer 137 may be disposed on the first light emitting layer 131A, a charge generation layer 133 may be disposed on the first electron transport layer 137, a second functional layer 135 may be located on the charge generation layer 133, a second light emitting layer 132A may be on the second functional layer 135, a second electron transport layer 134 may be disposed on the second light emitting layer 132A, and an electron injection layer 138 may be disposed on the second electron transport layer 134.

The first functional layer 136 may be formed of a plurality of layers such as, for example, a hole injection layer, a hole transport layer, and an electron blocking layer, which are sequentially stacked from one side surface of the substrate 110.

The second functional layer 135 may be formed of a plurality of layers and may be a layer in which a hole transport layer and an electron blocking layer are sequentially stacked from one side of the substrate 110 side, for example.

The encapsulation layer 150 may be disposed covering the organic light emitting diode element. The encapsulation layer 150 may be formed of an inorganic material such as SiOx and SiNx, although the present disclosure is not limited thereto. Further, although FIG. 6 illustrates a configuration in which the encapsulation layer 150 is of a single layer, the encapsulation layer 150 may be formed of multiple layers. In such a circumstance, the encapsulation layer 150 may be configured such that an inorganic film and an organic film are alternately arranged, although not limited thereto.

Figure 7:
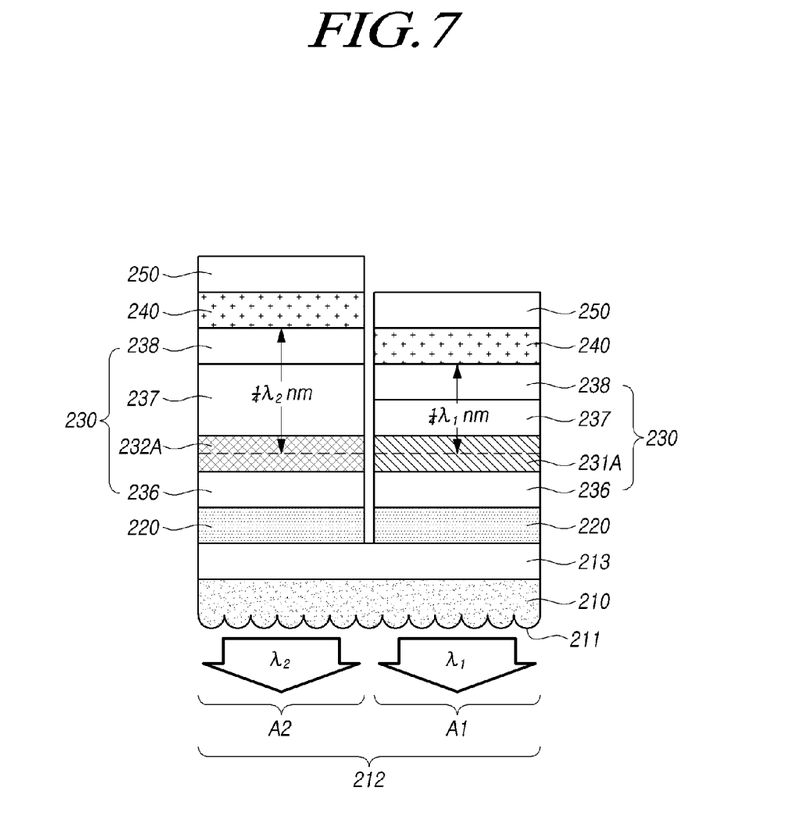

FIG. 7 shows a schematic cross-sectional view of a lighting device according to the aspects of the present disclosure.

Referring to FIG. 7, the lighting device according to aspects of the present disclosure may include a substrate 210, a first electrode 220, an organic material layer 230, a second electrode 240, and an encapsulation layer 250. Here, FIG. 7 illustrates that the organic material layer 230, the second electrode 240 and the encapsulation layer 250 are each spaced apart in the middle of the active region 212, but the organic material layer, the second electrode 240 and the encapsulation layer 250 that are not formed by patterning, may be formed as one continuous layer without being spaced apart in the middle portion of the active region 212.

A plurality of protrusions 211 may be integrally arranged on the back surface of the substrate 210, and the plurality of protrusions 211 may be formed so that the shape in a first area A1 is different from that in a second area A2. For example, the plurality of protrusions 211 in the first area A1 may have the shape optimized to extract the light with the first wavelength λ1 to the outside of the lighting device, while the plurality of protrusions 211 in the second area A2 may have the shape optimized to extract the light with the second wavelength λ2 to the outside of the lighting device. Since the first wavelength λ1 and the second wavelength λ2 may be different from each other, the plurality of protrusions 211 may also have different shapes in the first region A1 and in the second region A2.

The organic material layer 230 may include a first light emitting layer 231A and a second light emitting layer 232A.

Here, the first light emitting layer 231A and the second light emitting layer 232A may be patterned. A certain light emitting layer being patterned may mean that the light emitting layer may be formed with a specific pattern by a patterning process.

The patterned first light emitting layer 231A may be formed in the first area A1, and the patterned second light emitting layer 232A may be formed in the second area A2. In other words, the patterned first light emitting layer 231A may not be formed in the second region A2, and the patterned second light emitting layer 232A may not be formed in the first region A1. Referring then to FIG. 7, the first light emitting layer 231A may be positioned in the first area A1 while not positioned in the second area A2, and the second light emitting layer 232A may be positioned in the second area A2 while not positioned in the first area A1.

The first area A1 and the second area A2 may not overlap each other. Therefore, referring to FIG. 7, as the first area A1 in which the first light emitting layer 231A is formed and the second area A2 in which the second light emitting layer 232A is formed, do not overlap each other, the first light emitting layer 231A may be positioned not to overlap the second light emitting layer 232A.

The lighting device may include a first light emitting area emitting light with a first wavelength λ1 in the active area, and a second light emitting area emitting light with a second wavelength λ2.

When the first light emitting layer 231A and the second light emitting layer 232A are formed by patterning as described above, the light having the first wavelength λ1 is not absorbed into the first dopant included in the second light emitting layer 232A, even if the light having the first wavelength λ1 is emitted from the first light emitting layer 231A. As a result, the lighting device can produce a very excellent light output even for the light with the first wavelength λ1, thereby providing an excellent cosmetic effect on the skin.

For improving the intensity of light emitted from the first light emitting layer 231A by the micro-cavity effect, the distance between the first light emitting layer 231A and the second electrode 240 may be 0.20 to 0.30 times the first wavelength. The abovementioned range may be, for example, 0.22 to 0.28 times or 0.24 to 0.26 times the first wavelength. Alternatively, the distance between the first light emitting layer 231A and the second electrode 240 may be substantially 0.25 times the first wavelength. The distance between the first light emitting layer 231A and the second electrode 240 may represent a distance from the center of the first light emitting layer 231A to the reflective surface of the second electrode 240, and the first wavelength in the aforementioned distance may be a wavelength of the light with the strongest intensity when measuring the light emitted from the first light emitting layer 231A.

For enhancing the intensity of the light emitted from the second light emitting layer 232A by the micro-cavity effect, the distance between the second light emitting layer 232A and the second electrode 240 may be 0.20 to 0.30 times the second wavelength. Advantageously, the abovementioned range may be, for example, 0.22 to 0.28 times or 0.24 to 0.26 times the second wavelength. Alternatively, the distance between the second light emitting layer 232A and the second electrode 240 may be substantially 0.25 times the second wavelength. The distance between the second light emitting layer 232A and the second electrode 240 may designate a distance extending from the center of the second light emitting layer 232A to the reflective surface of the second electrode 240, and the second wavelength in the aforementioned distance may be a wavelength of the light with the strongest intensity when measuring the light emitted from the second light emitting layer 232A.

The organic material layer 230 may include other organic material layers, in addition to the first light emitting layer 231A and the second light emitting layer 232A. As an example, a first functional layer 236 may be disposed on the first electrode 220, light emitting layers 231A and 232A may be disposed on the first functional layer 236, an electron transport layer 237 may be disposed on the light emitting layers 231A and 232A, and an electron injection layer 238 may be located on the electron transport layer 237, sequentially.

The first functional layer 236 may be formed of a plurality of layers, such as, for example, a hole injection layer, a hole transport layer, and an electron blocking layer, sequentially stacked from one side surface of the substrate 210.

The electron transport layer 237 may be arranged between the first light emitting layer 231A and the second electrode 240 and between the second light emitting layer 232A and the second electrode 240.

The thickness of the electron transport layer 237 may be thicker in the second area A2 than in the first area A1. Referring to FIG. 7, it is seen that the thickness of the electron transport layer portion disposed in the second area A2 is larger than that of the electron transport layer portion disposed in the first area A1. When the electron transport layer 237 has the thickness as described above, it is possible to secure a cavity length in the second light emitting layer emitting the second wavelength longer than the first wavelength, for example.

It should be noted that the details of the substrate 210, the first electrode 220, the organic material layer 230, the second electrode 240, and the encapsulation layer 250 may be substantially the same as those described respectively for the substrate 110, the first electrode 120, the organic material layer 130, the second electrode 140 and the encapsulation layer 150, unless otherwise specifically described.

Figure 8:
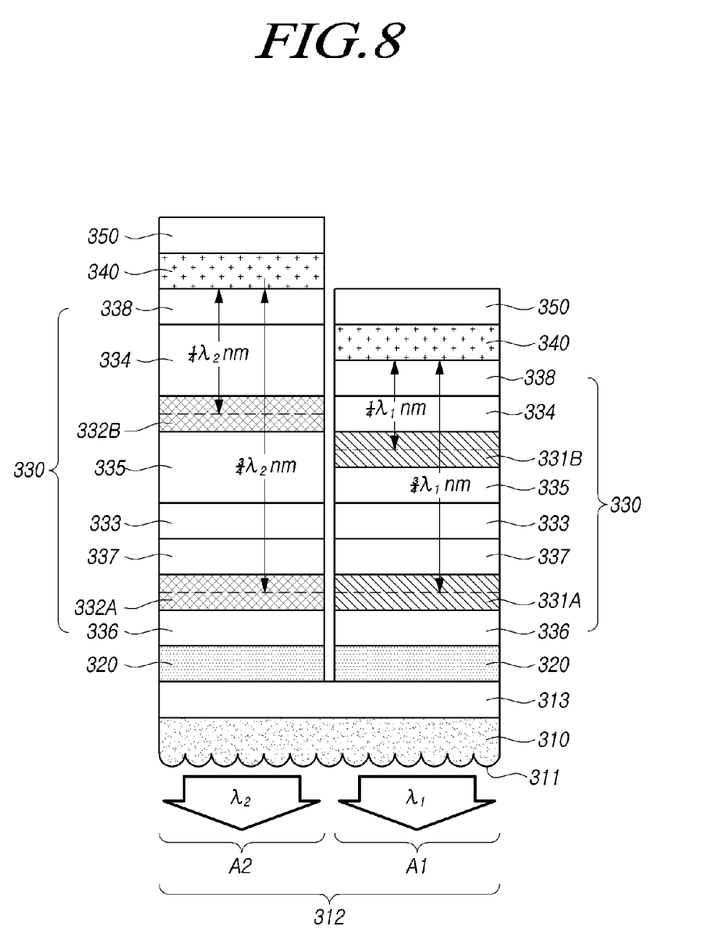

FIG. 8 shows a schematic cross-sectional view of a lighting device according to the aspects of the present disclosure.

Referring to FIG. 8, the lighting device according to the aspects of the present disclosure may include a substrate 310, a first electrode 320, an organic material layer 330, a second electrode 340, and an encapsulation layer 350. Although FIG. 8 illustrates that the organic material layer 330, the second electrode 340, and the encapsulation layer 350 are shown as being spaced apart in the middle of the active region 312, each of the organic material layer, the second electrode 340 and the encapsulation layer 350, which are not formed by patterning, may be formed as one continuous layer without getting split in the middle portion of the active region 312.

The organic material layer 330 may further include a first light emitting layer 331A and a second light emitting layer 332A.

The organic material layer 330 may include a third light emitting layer 331B and a fourth light emitting layer 332B. The light emitted by the third light emitting layer 331B may have a first wavelength, and the light emitted by the fourth light emitting layer 332B may have a second wavelength. In some aspects, the light emitted from the first light emitting layer 331A and the third light emitting layer 331B may have a wavelength corresponding to the first wavelength, which is a certain wavelength falling in the range corresponding to the first wavelength. Likewise, the light emitted from the second light emitting layer 332A and the fourth light emitting layer 332B may have a wavelength corresponding to the second wavelength, the relationship of which may be similar to that described above having regard to the first wavelength.

In case where the organic material layer 330 includes the first light emitting layer 331A and the third light emitting layer 331B that emit the light having the first wavelength, and the second light emitting layer 332A and the fourth light emitting layer 332B that emit the light having the second wavelength, it can further improve the outputs for both the light with the first wavelength and the light with the second wavelength.

The fourth light emitting layer 332B may include a second dopant that absorbs the light having the first wavelength and emits the light having the second wavelength. The second dopant may be substantially the same as or different from the first dopant described above.

The second dopant may be Pt(TPBP) (Pt-tetraphenyltetrabenzoporphyrin).

The first light emitting layer 331A, the second light emitting layer 332A, the third light emitting layer 331B, and the fourth light emitting layer 332B may be patterned. Patterning of a light emitting layer means that the light emitting layer may be formed with a specific pattern by a patterning process.

The patterned first light emitting layer 331A and the patterned third light emitting layer 331B may be formed in the first area A1, and the patterned second light emitting layer 332A and the patterned fourth light emitting layer 332B may be formed in the second area A2. In other words, the patterned first light emitting layer 331A and the patterned third light emitting layer 331B may be not formed in the second area A2, and the patterned second light emitting layer 332A and the patterned fourth light emitting layer 332B may be not formed in the first area A1. Referring then to FIG. 8, it is seen that the first light emitting layer 331A and the third light emitting layer 331B may be located in the first area A1 while not located in the second area A2, and the second light emitting layer 332A may be located in the second area A2 while not located in the first area A1.

The first area A1 and the second area A2 may not overlap each other. Therefore, referring to FIG. 8, it is seen that since the first region A1, in which the first light emitting layer 331A and the third light emitting layer 331B are formed, and the second area A2, in which the second light emitting layer 332A and the fourth light emitting layer 332B are formed, do not overlap each other, the first light emitting layer 331A may be positioned not to overlap the second light emitting layer 332A and the fourth light emitting layer 332B, and the third light emitting layer 331B may be positioned not to overlap the second light emitting layer 332A and the fourth light emitting layer 332B.

When those first to fourth light emitting layers 331A to 332B are formed by patterning as described above, and even if emission of the light with the first wavelength $\lambda 1$ is made in the first light emitting layer 331A and the third light emitting layer 331B, then the light with the first wavelength $\lambda 1$ will be not absorbed into the first dopant included in the second light emitting layer 332A and the second dopant included in the fourth light emitting layer 332B. As a result, the lighting device can provide excellent light output even for the light having the first wavelength $\lambda 1$, thereby rendering very excellent skin caring effects on the skin.

In order to improve the intensity of light emitted from the first light emitting layer 331A by the micro-cavity effect, the distance between the first light emitting layer 331A and the second electrode 340 may be 0.70 to 0.80 times the first wavelength. Advantageously, the above-mentioned range may be, for example, 0.72 to 0.78 times or 0.74 to 0.76 times the first wavelength. Alternatively, the distance between the first light emitting layer 331A and the second electrode 340 may be substantially 0.75 times the first wavelength. The distance between the first light emitting layer 331A and the second electrode 340 may mean a distance from the center of the first light emitting layer 331A to the reflective surface of the second electrode 340, and the first wavelength in the abovementioned distance may be a wavelength of the light having the strongest intensity when measuring the light emitted from the first light emitting layer 331A.

In order to improve the intensity of light emitted from the second light emitting layer 332A by the micro-cavity effect, the distance between the second light emitting layer 332A and the second electrode 340 may be 0.70 to 0.80 times the second wavelength. The above-mentioned range may be, for example, 0.72 to 0.78 times or 0.74 to 0.76 times the second wavelength. Alternatively, the distance between the second light emitting layer 332A and the second electrode 340 may be substantially 0.75 times the second wavelength. The distance between the second light emitting layer 332A and the second electrode 340 may mean the distance from the center of the second light emitting layer 331A to the reflective surface of the second electrode 340, and the second wavelength in the above distance may be a wavelength of the light having the strongest intensity when measuring light emitted from the second light emitting layer 332A.

For further improving the intensity of light emitted from the third light emitting layer 331B by the micro-cavity effect, the distance between the third light emitting layer 331B and the second electrode 340 may be approximately 0.20 to 0.30 times the first wavelength. The aforementioned range may be, for example, 0.22 to 0.28 times or 0.24 to 0.26 times the first wavelength. Alternatively, the distance between the third light emitting layer 331B and the second electrode 340 may be substantially 0.25 times the first wavelength. The distance between the third light emitting layer 331B and the second electrode 340 may mean a distance from the center of the third light emitting layer 331B to the reflective surface of the second electrode 340, and the first wavelength in the above-mentioned distance may be a wavelength of the light having the strongest intensity when measuring the light emitted from the third light emitting layer 331B.

For further improving the intensity of light emitted from the fourth light emitting layer 332B by the micro-cavity effect, the distance between the fourth light emitting layer 332B and the second electrode 340 may be about 0.20 to 0.30 times the second wavelength. The aforementioned range may be, for example, 0.22 to 0.28 times or 0.24 times to 0.26 times as the second wavelength. Alternatively, the distance between the fourth light emitting layer 332B and the second electrode 340 may be substantially 0.25 times the second wavelength. The distance between the fourth light emitting layer 332B and the second electrode 340 may mean a distance from the center of the fourth light emitting layer 332B to the reflective surface of the second electrode 340, and the second wavelength in the above-mentioned distance may be a wavelength of the light having the strongest intensity when measuring light emitted from the fourth light emitting layer 332B.

The organic material layer 330 may include other organic material layers in addition to the aforementioned first to fourth light emitting layers 331A to 332B. For example, a first functional layer 336 may be disposed on a first electrode 320, the light emitting layers 331A and 332A may be disposed on the first functional layer 336, a first electron transport layer 337 may be disposed on the light emitting layers 331A and 332A, a charge generation layer 333 may be disposed on the first electron transport layer 337, a second functional layer 335 may be disposed on the charge generation layer 333, the light emitting layers 331B and 332B may be disposed on the second functional layer 335, a second electron transport layer 334 may be disposed on the light emitting layers 331B and 332B, and an electron injection layer 338 may be disposed on the second electron transport layer 334, sequentially.

The first functional layer 336 may be formed of a plurality of layers, such as, for example, a hole injection layer, a hole transport layer, and an electron blocking layer sequentially stacked from one side of the substrate 310.

The organic material layer may include two electron transport layers as described above. The first electron transport layer 337 may be positioned between the first light emitting layer 331A and the charge generation layer 333, and between the second light emitting layer 332A and the charge generation layer 333. Further, the second electron transport layer 334 may be positioned between the third light emitting layer 331B and the second electrode 340 and between the fourth light emitting layer 332B and the second electrode 340.

The thickness of the second electron transport layer 334 may be thicker in the second region A2 than in the first region A1. Referring now to FIG. 8, the thickness of a portion of the second electron transport layer 334 located on the second area A2 may be greater than the thickness of a portion of the second electron transport layer 334 located on the first area A1. When the second electron transport layer 334 has the thickness as described above, it can secure a cavity length of the second light emitting layer and the fourth light emitting layer for emitting the second wavelength longer than the first wavelength, for example.

The second functional layer 335 may be formed of a plurality of layers, such as, for example, a hole transport layer and an electron blocking layer sequentially stacked from one side of the substrate 310.

The second functional layer 335 may be positioned between the first light emitting layer 331A and the third light emitting layer 331B and between the second light emitting layer 332A and the fourth light emitting layer 332B. Alternatively, the second functional layer 335 may be positioned between the charge generation layer 333 and the third light emitting layer 331B and between the charge generation layer 333 and the fourth light emitting layer 332B. Thus, the second functional layer 335 disposed at the aforementioned position may serve to transmit the holes to the third light emitting layer 331B and the fourth light emitting layer 332B.

The thickness of the second functional layer 335 may be thicker in the second area A2 than in the first area A1. Referring to FIG. 8, it is seen that the thickness of a portion of the second functional layer 335 positioned in the second area A2 may be greater than that of a portion of the second functional layer 335 positioned in the first area A1. When the second functional layer 335 has the thickness as described above, it can be secured a cavity length of the second light emitting layer and the fourth light emitting layer emitting the second wavelength longer than the first wavelength, for example.

The thickness of the second functional layer 335 may stand for the total thickness of the whole second functional layer 335. At least one layer of a plurality of layers constituting the second functional layer 335 may have a thicker thickness in the second area A2 than the first area A1. As an example, the thickness of the layer, notwithstanding with the larger thickness, having a relatively small degree of increase in the driving voltage of the organic light emitting diode element, among several layers constituting the second functional layer 335, can be increased in the second area A2. For example, the thickness of the hole transport layer among a plurality of layers constituting the second functional layer 335 may be formed thicker in the second area A2 to secure a cavity length as required.

The details of the substrate 310, the first electrode 320, the organic material layer 330, the second electrode 340, and the encapsulation layer 350 may be substantially the same as those described above for the substrate 110, the first electrode 120, the organic material layer 130, the second electrode 140 and the encapsulation layer 150, unless otherwise specifically described therefor.

Figure 9:
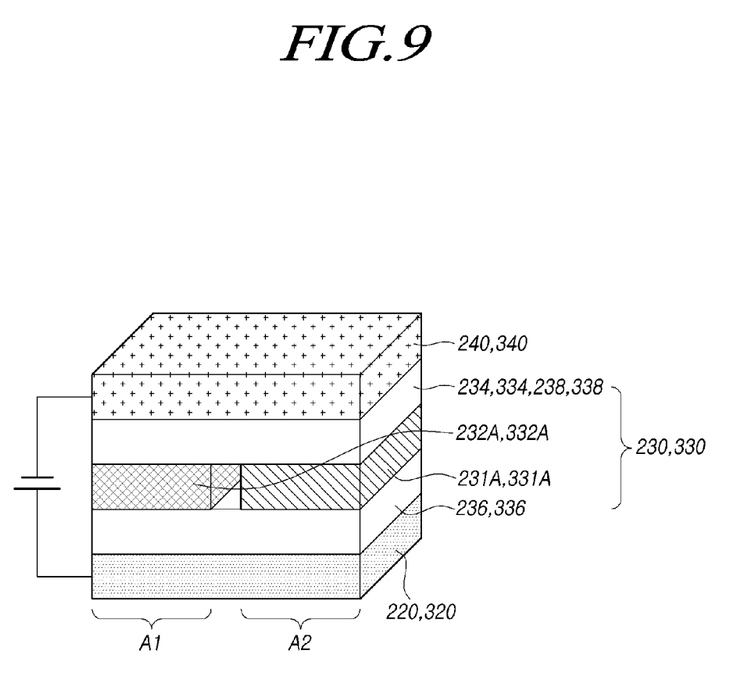
FIGS. 9 and 10 each are views for illustrating the arrangement of the first electrode in the lighting device according to the present disclosure.

FIG. 9 shows a schematic diagram for explaining the aspects of the present disclosure in which light emitting layers 231A, 331A, 232A, and 332A are formed by patterning, and first electrodes 220 and 320 are commonly formed in a first area A1 and a second area A2.

Although not illustrated in FIG. 9, the aspects to be described with reference thereto may further include aspects including a third light emitting layer formed by patterning an organic material layer and a fourth light emitting layer formed by such patterning.

Referring then to FIG. 9, an organic light emitting element may be driven by applying voltages to the first electrodes 220 and 320 and the second electrodes 240 and 340. When an electrode commonly formed in the first area A1 and the second area A2 is used as the first electrodes 220 and 320, a ratio of the areas in the first area A1 and the second area A2 can be adjusted to control the intensity of light with a first wavelength and the intensity of light with a second wavelength for irradiation onto the skin.

As an example, the ratio of the first area A1 to the second area A2 may be approximately 1:9 to 9:1. By adjusting the areas of the first area A1 and the second area A2 in the above-described range, it is possible to provide a lighting device with a maximized cosmetic effect.

Accordingly, in the aspects of the present disclosure in which the light emitting layer is formed by patterning, as described with reference to FIGS. 7 and 8, when the first electrodes 220 and 320 is a common electrode commonly formed across the first area A1 and the second area A2, it is possible to control the output of light having the first wavelength and the output of light having the second wavelength emitted from a controller, by adjusting the areas of the first area A1 and the second area A2.

Figure 10:
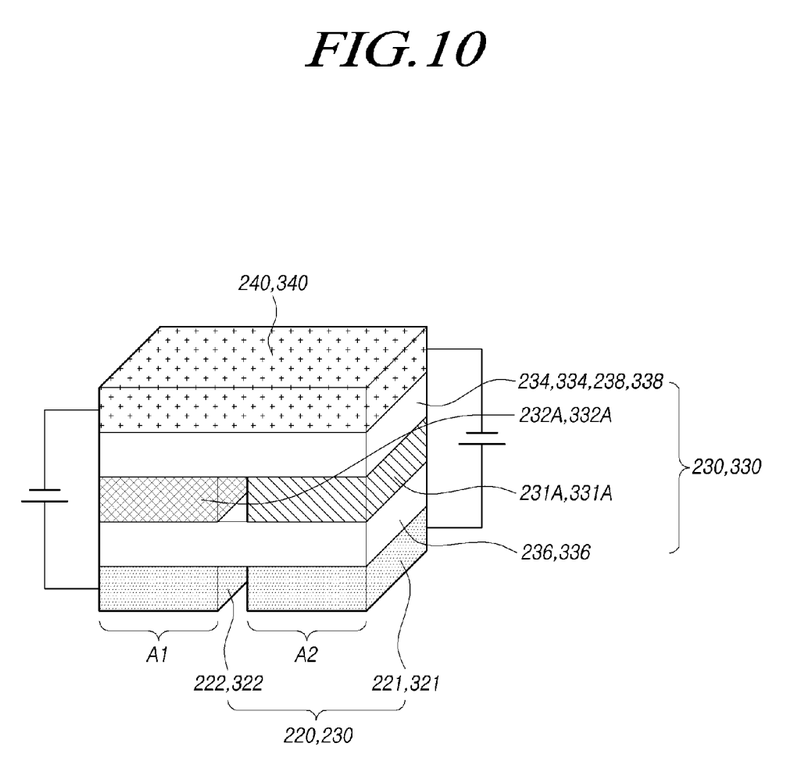

FIG. 10 shows a schematic diagram for explaining the aspects of the present disclosure, in which light emitting layers 231A, 331A, 232A and 332A are formed by patterning, and first electrodes 220 and 320 are formed by patterning in the first area A1 and the second area A2, respectively.

Although not illustrated in FIG. 10, the aspects to be described with reference thereto may further include aspects including a third light emitting layer formed by patterning an organic material layer and a fourth light emitting layer formed by such patterning.

Referring then to FIG. 10, in the lighting device according to the aspects of the present disclosure, the first electrodes 220 and 320 may include first area electrodes 221 and 321 formed in the first area and second area electrodes 222 and 322 formed in the second area.

When the first electrodes 220 and 320 include the first area electrodes 221 and 321 and the second area electrodes 222 and 322, the voltage applied to the first area electrodes 221 and 321 and the voltages applied to the second area electrodes 222 and 322 can be individually adjusted, so that it is possible to control the output of light having the first wavelength and the output of light having the second wavelength emitted from the lighting device, respectively.

Accordingly, in the lighting apparatus according to the aspects of the present disclosure formed by the patterned light emitting layer as described with reference to FIGS. 7 and 8, when the first electrodes 220 and 320 include the first area electrodes 221 and 321 and the second area electrodes 222 and 322, the lighting device can adjust the voltages applied to the first area electrodes 221 and 321 and the second area electrodes 222 and 322 to irradiate light more suited to the user's skin condition.

The above description has been presented to enable any person skilled in the art to make and use the technical idea of the present disclosure, and has been provided in the context of a particular application and its requirements. Various modifications, additions and substitutions to the described aspects will be readily apparent to those skilled in the art, and the general principles defined herein may be applied to other aspects and applications without departing from the spirit and scope of the present disclosure. The above description and the accompanying drawings provide an example of the technical idea of the present disclosure for illustrative purposes only. That is, the disclosed aspects are intended to illustrate the scope of the technical idea of the present disclosure. Thus, the scope of the present disclosure is not limited to the aspects shown, but is to be accorded the widest scope consistent with the claims. The scope of protection of the present disclosure should be construed based on the following claims, and all technical ideas within the scope of equivalents thereof should be construed as being included within the scope of the present disclosure.

What is claimed is:

1. A lighting device comprising:
a substrate including an active area;
a first electrode disposed on the substrate and including a transparent conductive material;
an organic material layer disposed on the first electrode and including a first light emitting layer and a second light emitting layer; and
a second electrode disposed on the organic material layer and including a reflective material,
wherein the first light emitting layer emits light having a first wavelength and the second light emitting layer emits light having a second wavelength,
wherein the second light emitting layer includes a first dopant absorbing the light having the first wavelength and emitting the light having the second wavelength,
wherein the first wavelength is in a range of between 630 nm to 700 nm and the second wavelength is in a range of more than 700 nm to 1000 nm or less, and
wherein the second light emitting layer is positioned closer to the second electrode than the first light emitting layer.

2. The lighting device according to claim 1, wherein the first dopant includes Pt(TPBP) (Pt-tetraphenyltetrabenzoporphyrin).

3. The lighting device according to claim 1, wherein the substrate has a plurality of protrusions integrally formed on a surface facing opposite to the organic material layer.

4. The lighting device according to claim 1, wherein the first and second light emitting layers are disposed over an entire active area of the substrate.

5. The lighting device according to claim 4, wherein a distance between the first light emitting layer and the second electrode is 0.70 and 0.80 times the first wavelength, and
wherein a distance between the second light emitting layer and the second electrode is 0.20 and 0.30 times the second wavelength.

6. A lighting device comprising:
a substrate including an active area;
a first electrode disposed on the substrate and including a transparent conductive material;
an organic material layer disposed on the first electrode and including a first light emitting layer and a second light emitting layer; and
a second electrode disposed on the organic material layer and including a reflective material,
wherein the first light emitting layer emits light having a first wavelength and the second light emitting layer emits light having a second wavelength,
wherein the first light emitting layer is disposed in a first area, and the second light emitting layer is disposed in a second area, and
wherein the first area and the second area are separated from each other and do not overlap with each other, and
wherein the first wavelength is in a range of between 630 nm to 700 nm and the second wavelength is in a range of more than 700 nm to 1000 nm or less.

7. The lighting device according to claim 6, wherein a distance between the first light emitting layer and the second electrode is 0.20 to 0.30 times the first wavelength, and
wherein a distance between the second light emitting layer and the second electrode is 0.20 to 0.30 times the second wavelength.

8. The lighting device according to claim 6, wherein the organic material layer further comprises an electron transport layer,
wherein the electron transport layer is disposed between the first light emitting layer and the second electrode and between the second light emitting layer and the second electrode, and
wherein the electron transport layer has a thickness in the second area greater than in the first area.

9. The lighting device according to claim 6, wherein the first electrode is disposed over an entire active area of the substrate.

10. The lighting device according to claim 6, wherein the first electrode includes a first area electrode disposed in the first area and a second area electrode disposed in the second area.

11. The lighting device according to claim 6, wherein the organic material layer further comprises a third light emitting layer that emits light having the first wavelength and a fourth light emitting layer that emits light having the second wavelength,
wherein the first light emitting layer and the third light emitting layer are disposed in the first area, and
wherein the second light emitting layer and the fourth light emitting layer are disposed in the second area.

12. The lighting device according to claim 11, wherein a distance from the first light emitting layer to the second electrode is 0.70 to 0.80 times the first wavelength,
wherein a distance from the second light emitting layer to the second electrode is 0.70 to 0.80 times the second wavelength,
wherein a distance from the third light emitting layer to the second electrode is 0.20 to 0.30 times the first wavelength, and
wherein a distance from the fourth light emitting layer to the second electrode is 0.20 to 0.30 times the second wavelength.

13. The lighting device according to claim 11, wherein the organic material layer further comprises an electron transport layer disposed between the third light emitting layer and the second electrode, and between the fourth light emitting layer and the second electrode, and
wherein the electron transport layer has a thickness in the second area greater than in the first area.

14. The lighting device according to claim 11, wherein the organic material layer further comprises a functional layer disposed between the first light emitting layer and the third light emitting layer and between the second light emitting layer and the fourth light emitting layer, and
wherein functional layer has a thickness in the second area greater than in the first area.

15. The lighting device according to claim 11, wherein the first electrode is disposed over an entire active area of the substrate.

16. The lighting device according to claim 11, wherein the first electrode is formed by patterning and includes a first area electrode formed in the first area and a second area electrode formed in the second area.

* * * * *